United States Patent [19]

Newman et al.

[11] Patent Number: 4,708,765

[45] Date of Patent: Nov. 24, 1987

[54] REGULATION OF THE EXPOSURE OF ACTIVE SURFACES

[75] Inventors: Arnold L. Newman, Kensington; William D. Stanbro, Columbia, both of Md.

[73] Assignee: The Johns Hopkins University, Baltimore, Md.

[21] Appl. No.: 915,602

[22] Filed: Oct. 6, 1986

[51] Int. Cl.[4] .................. B44C 1/22; C03C 15/00; C03C 25/06
[52] U.S. Cl. .................................. 156/626; 156/655; 156/668; 156/345
[58] Field of Search ............... 156/345, 626, 655, 668

[56] References Cited

U.S. PATENT DOCUMENTS

| | | | |
|---|---|---|---|
| 3,523,842 | 8/1970 | Glendinning | 156/345 X |
| 4,384,917 | 5/1983 | Wensink | 156/627 |
| 4,528,063 | 7/1985 | Lawrence et al. | 156/626 |

Primary Examiner—William A. Powell
Attorney, Agent, or Firm—Robert E. Archibald; Mary L. Beall

[57] ABSTRACT

This invention relates to an apparatus and method for regulating the exposure of active surfaces by covering the surface with an erodible protection coating. The rate of erosion is controlled by chemical and/or physical means so that the surface is progressively and gradually exposed.

60 Claims, 5 Drawing Figures

REGULATION OF THE EXPOSURE OF ACTIVE SURFACES

STATEMENT OF GOVERNMENTAL INTEREST

The Government has rights in this invention pursuant to Contract No. N00024-85-C-5301 awarded by the Department of the Navy.

BACKGROUND OF THE INVENTION

This invention relates to an apparatus and method for regulating the exposure of an active surface. In particular, this method and apparatus are used to detect the presence of pollutants and toxins in the environment.

U.S. Pat. No. 4,115,067 and 4,032,297 both describe a pollutant gas-sensitive substrate in the form of an elongated strip that can be intermittently advanced to provide a series of fresh, light-reflective surfaces sensitive to the pollutant gas. The pollutant gas reacts with the surface causing a decrease in the reflectivity thereof. Measuring a decrease in the light-reflectivity serves to indicate the concentration of the pollutant gas.

U.S. Pat. No. 4,338,094 discloses a process for detecting antigens in a biological sample wherein a particulate supported antibody is loosely encapsulated or confined within a porous filter membrane material. The liquid biological sample can pass through the porous membrane to react with the antibody.

U.S. Pat. No. 4,234,316 relates to a device for delivering measured quantities of a plurality of water soluble reagents to an assay medium. Each reagent is incorporated in a carrier binder. By choosing binders that dissolve or disburse in water at different rates, a rate of reagent delivery as well as the sequence of delivery of different reagents can be controlled. A list of carrier materials is provided.

U.S. Pat. No. 4,434,153 discloses a time release delivery device for beneficial drugs. The materials forming the device wall can be selected to release the drug by different physical-chemical mechanisms such as erosion, diffusion, osmosis, and metabolism. The outer wall of the device can also be provided with various thicknesses as an additional aid for providing timed release of the drug.

U.S. Pat. No. 4,225,575 relates to a device for conducting chemical reactions at a liquid-solid interface. A reaction component is fixed on the surface of a dip stick type device to be immersed in a second liquid reaction component. No protective surface is provided for the fixed reaction component.

Other U.S. patents relating to the release of a reagent are U.S. Pat. Nos. 4,188,447; 4,275,031 and 4,448,548. Additionally, U.S. Pat. No. 4,260,392 relates to a reagent impregnated gel.

OBJECTS OF THE INVENTION

It is an object of the present invention to produce a method and apparatus to regulate the exposure of an active surface.

It is also an object of the present invention to produce a method and apparatus to progressively and continuously provide a reactive surface.

It is also an object of the present invention to produce a method and apparatus for the continuous detection of pollutants and toxins.

Another object of the present invention is a method and apparatus wherein a fresh, unpoisoned reactive surface is always available and further wherein the surface is protected until needed.

SUMMARY OF THE INVENTION

This invention relates to an erodible, soluble or otherwise dispersable coating covering an active surface. The function of the coating is to protect and preserve the surface. A critical feature of this invention is that the exposed coating is not a reagent to be released into the aqueous or fluid medium to participate in the chemical reaction. Only when the coating erodes or disperses through the action of the environment, is the reactive surface exposed and the desired reaction allowed to proceed on the surface or assisted by the surface.

The erosion or dissolution rate of the coating can be controlled by physical and/or chemical means. For example, if the coating is water soluble, it can be applied to the surface with a gradually increasing thickness. Water flowing over the coating will dissolve the thinner portions first and the active surface thereunder will be exposed before surface areas covered by a thicker coating.

An example of a physical erosion mechanism is the erosion of a silicone rubber coating in an environment containing an abrasive material such as clay.

Chemical erosion mechanisms include, for example, the dissolution of starch by amylase hydrolysis in the presence of water. In this system, the protective coating comprises starch and amylase enzyme in the dry state. When water flows over the coating, the amylase hydrolyses the starch and thus chemically removes the coating.

The combination of physical and chemical erosion is exemplified by a protective coating comprising a phospholipid layer made with unsaturated fatty acids and hematoporphyrin. In the presence of light, the hematoporphyrin converts oxygen ($O_2$) to singlet oxygen ($'\Delta_g O_2$) which then attacks the double bonds of the lipid to destroy the lipid layer and expose the active macroreticular resin layer.

Specific erosion modulators are, for example, a gradually increasing thickness of the coating and a gradually increasing concentration of a slowly dissolving substance within the coating. Also, by gradually increasing the level of polymerization, within the coating, the erosion rate can be controlled. The erosion process may also be modulated by the chemical and/or physical composition of the eroding medium as well as factors such as heat, ultrasonic energy and pH.

This invention has particular application where it is necessary to regulate the exposure of surface concentrating and/or reacting agents. Examples of surface concentrating agents are antigens, antibodies, receptors, lectins and ion exchange resins having application in chromatography and sensors. Examples of reacting agents are macroreticular resins, zeolites, catalysts, enzymes and living cells that can be used in catalytic reaction beds and fluidized matrix columns. Many of these continuous flow systems are very sensitive to changes in ambient conditions such as temperature and pH, which can adversely affect the reactive surface. Moreover, reactions on the chemically reactive surface also can be compromised by poisoning caused by the products of the chemical reaction itself. Enzymes and solid catalysts such as platinum, palladium and nickel catalyze only when appropriate reactants contact the catalytic surface. Furthermore, immobilized antibodies will bind only when the specific antigen or hapten is presented to the antibody bonding site. In other words, for such systems to function, a reacting or concentrating surface must be clean and available.

According to the present invention, a fresh chemically reactive surface is always presented to the reactants. There are two main benefits:

1. The amount of reactive surface material is conserved in the event of a sudden loss of the reactive moiety of the surface due to environmental changes.

2. In the event of enzyme of catalyst poisoning by the products of reaction, another reactive surface is soon available.

The present invention is not limited to aqueous or other fluid systems but includes coatings made of solid materials that sublimate to expose the reactive surface. The following is a partial list of materials suitable for use as protective coatings in the present invention:

dextran, polyacrylamide, polyacrylic acid and its salts, polyvinyl alcohol, polyethylene glycol, polyethylene oxide, polyvinylpyrrolidone, clarified guar gum, carboxymethyl cellulose, hydroxyethyl cellulose, methyl cellulose, algin, carrageenan, xanthan gum, and starch as described in U.S. Pat. No. 4,234,316. Copolymers of maleic anhydride with various vinyl monomers as described, for example, in U.S. Pat. No. 2,047,398, particularly copolymers of maleic anhydride with vinyl ether, or vinyl ester, or their corresponding salts can be used. Non-polymeric barriers such as those composed of sorbitol, potassium sodium tartrate, mannose and sucrose are also suitable.

DESCRIPTION OF THE PREFERRED EMBODIMENTS

Figure 1:
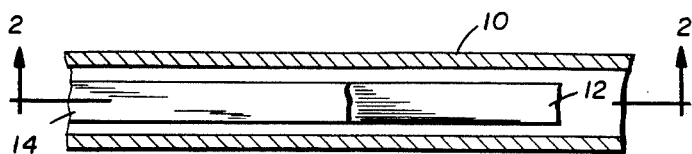
FIG. 1 is a tube containing a paper test strip covered with a chemically reactive surface.
Figure 2:
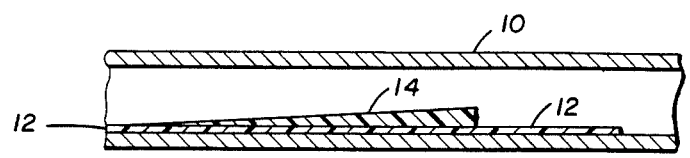
FIG. 2 is a cross-sectional view of FIG. 1 taken along line 2—2.

A major use for the method and apparatus of the present invention is to detect the presence of substances such as microorganisms and/or chemicals in a gaseous or liquid environment. In FIGS. 1 and 2, fluid from the environment continuously flows through tube 10. An elongated strip of pH sensitive paper 12 is fixed to the bottom of the tube. The presence of acid within tube 10 causes the pH sensitive paper to change color. An erodible sugar coating or barrier 14 having a gradually increasing thickness covers pH sensitive strip 12. As the fluid sample flows through tube 10, it erodes or wears away coating 14. Since some portions of coating 14 are not as thick as others, these portions are the first to be completely eroded to expose part of the surface of the pH sensitive strip 12. With the passage of time, the thicker portions of protective coating 14 are gradually worn away, increasing the amount of reactive surface available. Thus, a record of the pH conditions indicating the amount of acid, if any, in the environment over a period of time, is made. The color change at the freshly exposed surface can be monitored by a photosensitive cell.

Such a device is useful in the environmental detection and control of acid in the outflow of industrial paper manufacturing. It is also useful to detect the presence of acid in rain when installed outdoors in an inclined position.

Figure 3:
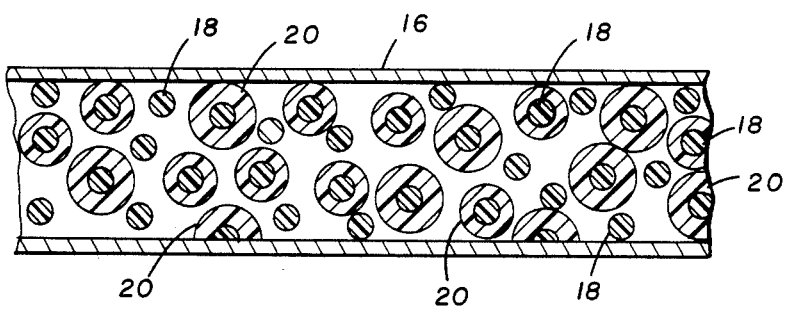
FIG. 3 is a packed column in which spherical reactive surfaces are protected with coatings of varying thicknesses.

FIG. 3 represents a packed column 16 filled with zeolite particles 18. Most immobilized particles are provided with a gelatin coating 20 to protect the active surface. The thickness of each coating 20 varies. As fluid flows through the column 16, coating 20 gradually wears away, the thinnest coatings disappearing first.

This particular embodiment relates to a water softening device wherein $Ga^{++}$ ions are removed and replaced with $Na^+$ ions provided by the zeolite particles 18. In this ion exchange process, not all the active surfaces are immediately available for reaction with $Ca^{++}$ ions in the incoming water since the active surface of the coated zeolite particles only becomes available as gelatin coating 20 wears away. As the water flows through the packed column, the $Na^+$ ions on the available active surfaces are replaced with $Ca^{++}$ ions and, at the same time, new active surfaces are made available through erosion of the thicker protective coating. Thus, this device provides a steady rate of replacement of $Ca^{++}$ ions with $Na^+$ ions. If there was no sequential availability of active surfaces, the replacement rate would be high at the beginning of service of the packed column decreasing to almost nothing at the end.

Figure 4:
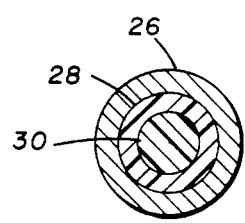
FIG. 4 is cross-section of a spherical support covered with a surface active agent that is in turn covered by an erodible layer.
Figure 5:
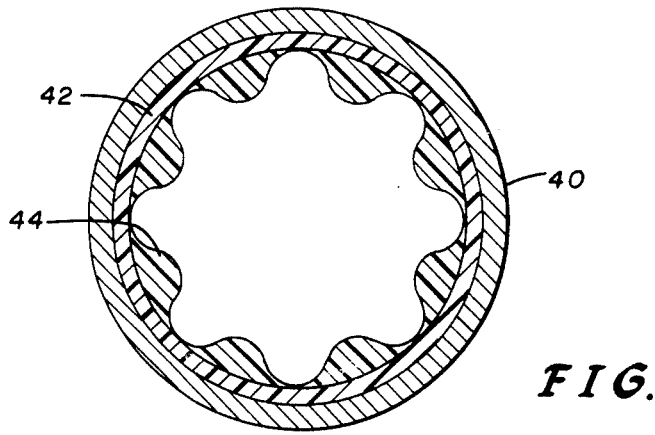
FIG. 5 is a cross-section of a tubular flow-through reactor wherein the reactive surface is provided with a coating of variable thickness.

FIGS. 4 and 5 are different embodiments of substrates having active surfaces protected by erodible coatings. FIG. 4 is cross-section of a spherical support 30 covered by active surface 28. Erodible coating 26 protects active surface 28 until the coating has been worn away by the effects of the particular environment. In order to constantly expose a fresh or new active surface according to the process and apparatus of the present invention, many such spherical particles are used in the same reactive process and the thickness of the protective coating varies from particle to particle.

FIG. 5 is a cross-section of a tubular support 40, the inside surface thereof provided with active surface 42. Protective coating 44, having an undulating surface, allows increasing amounts of the active surface 42 to be exposed by the action of fluid passing through tube 40. This particular embodiment is useful for biological reactions wherein the biologically active microorganism covalently bound to the interior of tubular support 40 is the active surface and is covered with protective coating 44. In a particular example, alcohol is produced through the action of yeast covalently bound to the interior of tubular support 40 by fermentation of the substrate flowing through the tube. The action of the substrate moving through the tube also gradually erodes sugar coating 44. When the concentration of the alcohol reaches approximately 15%, the yeast begins to die. However, with a constantly increasing supply of fresh yeast being provided as the sugar coating is eroded, the amount of alcohol produced can be increased and sustained.

Biological reactions can also be used to detect the presence of toxins in an environment. For example, to detect the presence of the gastroenteritis causing toxin of *Salmonella enteritidis* in a food processing stream, a small portion of the stream is diverted through a tube for testing. At the entrance end of the tube, a mouse anti-Salmonella toxin antibody with a fluorescent tag is added to the diverted stream. If Salmonella toxin is present in this stream, it binds to the tagged antibody to form a tagged mouse anti-Salmonella toxin antibody/Salmonella toxin. The reactive surface located further down the tube is an immobilized antibody to this tagged antibody/toxin. If the tagged antibody/toxin is formed, it binds to the antibody immobilized on the surface and the fluorescent tage is detected by a photo-diode system. The reactive surface is elongated, similar to the paper test strip of FIG. 1. It is covered with a protective coating the thickness of which increases gradually along the length of the strip. The coating erodes in response to the flowing action of the diverted food stream and, thus, fresh reactive surfaces become available with time. An examination of the fluorescence at most recently exposed area provides a time based history of testing for Salmonella toxin contamination.

Another application of the present method and apparatus involves catalytic reactions such as those used to remove noxious elements from automobile exhaust gases. After a period of use, the surface of the catalytic layer has been coated with tar, residues and other components of the exhaust gas which completely coat or poison the catalyst. A catalyst according to the present application has a protective layer covering the catalytically active surface and, since the layer varies in thickness, only a small portion of the catalytic surface is available at a given time. Therefore, not all of the catalytic layer can be poisoned and a fresh catalytic portion will be made available with the passage of time.

In a variation of the present invention, the reactive surface is provided in strip form but is not continuous. A series of reactive bumps or particles are fixed to the surface, each bump being provided with its individual protective coating. The erosion rate of the coating is controlled by the appropriate physical and/or chemical means as discussed above.

The invention described is not intended to be limited to the embodiments disclosed but includes modifications made within the true spirit and scope of the invention.

What is claimed is:

1. A method of regulating the exposure of active surface comprising:
   a. providing an active surface;
   b. covering the active surface with an erodible protective coating;
   c. exposing the coated, active surface to the action of an environment comprising a medium able to erode the protective coating; and,
   wherein the nature of the coating varies so that first portions of the coating are eroded to expose the active surface portions thereunder before other portions are eroded, in such a way that portions of the active surface are progressively and gradually exposed as their respective coating portions are eroded.

2. A method according to claim 1, wherein the active surface is one of a surface concentrating agent and a surface reacting agent.

3. A method according to claim 1, wherein the active surface is one of an antigen, an antibody, a receptor, a lectin, an enzyme and a living cell.

4. A method according to claim 1, wherein the active surface is one of a macroreticular resin, a zeolite, a catalyst and an ion exchange resin.

5. A method according to claim 1, wherein the protective coating is selected from the group consisting of dextran, polyacrylamide, polyacrylic acid and its salts, polyvinyl alcohol, polyethylene glycol, polyethylene oxide, polyvinyl pyrrolidone, clarified guar gum, carboxymethyl cellulose, hydroxyethyl cellulose, methyl cellulose, algin, carrageenan, xanthan gum, starch, sorbitol, potassium sodium tartrate, mannose and sucrose.

6. A method according to claim 1, wherein the protective coating is a copolymer of maleic anhydride with a vinyl monomer.

7. A method according to claim 1, wherein the environment also comprises a substance able to react with the active surface.

8. An apparatus for regulating the exposure of active surfaces comprising:
   a. the active surface;
   b. an erodible protective non-uniform coating covering the active surface;
   c. means exposing the coated, active surface to the action of an environment comprising a medium able to erode the protective coating; and,
   wherein the nature of the coating varies so that first portions of the coating are eroded to expose the active surface portions thereunder before other portions are eroded in such a way that portions of the active surface are progressively and gradually exposed as their respective coating portions are eroded.

9. An apparatus according to claim 8, wherein the active surface is one of a surface concentrating agent and a surface reacting agent.

10. An apparatus according to claim 8, wherein the active surface is one of an antigen, an antibody, a receptor, a lectin, an enzyme and a living cell.

11. An apparatus according to claim 9, wherein the active surface is one of a macroreticular resin, a zeolite, a catalyst and an ion exchange resin.

12. An apparatus according to claim 9, wherein the protective coating is selected from the group consisting of dextran, polyacrylamide, polyacrylic acid and its salts, polyvinyl alcohol, polyethylene glycol, polyethylene oxide, polyvinylpyrrolidone, clarified guar gum, carboxymethyl cellulose, hydroxyethyl cellulose, methyl cellulose, algin, carrageenan, xanthan gum, starch, sorbitol, potassium sodium tartrate, mannose and sucrose.

13. An apparatus according to claim 1, wherein the protective coating is a copolymer of maleic anhydride with a vinyl monomer.

14. An apparatus according to claim 8, wherein the environment also comprises a substance able to react with the active surface.

15. A method of regulating the exposure of active surfaces comprising:
   a. providing an active surface;
   b. covering the active surface with an erodible protective coating;
   c. exposing the coated, active surface to the action of an environment comprising a medium able to erode the protective coating; and,
   wherein the thickness of the coating varies so that thinner portions of the coating are eroded to expose the active surface portions thereunder before thicker portions are eroded, in such a way that portions of the active surface are progressively and gradually exposed as their respective coating portions are eroded.

16. A method according to claim 15, wherein the surface is planar, the coating increases in thickness linearly from one end to the other end, and further wherein the reactive surface is first exposed at said one end and is progressively exposed moving towards said other end.

17. A method according to claim 15, wherein the surface is particulate, the thickness of the coating varies in thickness from particle to particle and further wherein the reactive surface is first exposed by eroding the thinner coatings and is progressively exposed as the thicker coatings are eroded.

18. A method according to claim 17, wherein the coated particulate surfaces are packed in a tube and the environment acts on the active surface by flowing from one end of the tube to the other.

19. A method according to claim 15, wherein the surface has a tube form, the surface and the coating are on the inside of the tube and the environment acts on the surface by flowing from one end of the tube to the other.

20. A method according to claim 15, wherein the environment also comprises a substance able to react with the active surface.

21. An apparatus for regulating the exposure of active surfaces comprising:
  a. an active surface;
  b. an erodible protective non-uniform coating covering the active surface;
  c. means exposing the coated, active surface to the action of an environment comprising a medium able to erode the protective coating; and,
wherein the thickness of the coating varies so that thinner portions of the coating are eroded to expose the active surface portions thereunder before thicker portions are eroded, in such a way that portions of the active surface are progressively and gradually exposed as their respective coating portions are eroded.

22. An apparatus according to claim 21, wherein the surface is planar, the coating increases in thickness linearly from one end to the other end, and further wherein the reactive surface is first exposed at said one end and is progressively exposed moving towards said other end.

23. An apparatus according to claim 21, wherein the surface is particulate, the thickness of the coating varies in thickness from particle to particle and further wherein the reactive surface is first exposed by eroding the thinner coatings and is progressively exposed as the thicker portions are eroded.

24. An apparatus according to claim 23, wherein the coated particulate surfaces are packed in a tube and the environment acts on the active surface by flowing from one end of the tube to the other.

25. An apparatus according to claim 21, wherein the surface has a tube form and the coating is on the inside of the tube.

26. An apparatus according to claim 21, wherein the environment also comprises a substance able to react with the active surface.

27. A method of regulating the exposure of active surfaces comprising:
  a providing an active surface;
  b. covering the active surface within an erodible protective coating;
  c. exposing the coated, active surface to the action of a environment comprising a medium able to erode the protective coating; and,
wherein the chemical composition of the coating varies so that first portions of the coating are eroded to expose the active surface portions thereunder before other portions are eroded, in such a way that portions of the active surface are progressively and gradually exposed as their respective coating portions are eroded.

28. A method according to claim 27, wherein the progressive and gradual exposure is controlled by gradually increasing the concentration of an erodible substance in the protective coating.

29. A method according to claim 27, wherein the protective coating comprises a polymer and further wherein the progressive and gradual exposure is controlled by gradually increasing the level of polymerization of the polymer in the protective coating.

30. A method according to claim 27, wherein the environment also comprises a substance able to react with the active surface.

31. An apparatus for regulating the exposure of active of surfaces comprising:
  a. the active surface;
  b. an erodible protective non-uniform coating covering the active surface;
  c. means exposing the coated, active surface to the action of an environment comprising a medium able to erode the protective coating; and,
wherein the chemical composition of the coating varies so that first portions of the coating are eroded to expose active surface portions thereunder before other portions are eroded, in such a way that portions of the active surface are progressively and gradually exposed as their respective coating portions are eroded.

32. An apparatus according to claim 31, wherein the concentration of an erodible substance in the protective coating increases gradually.

33. An apparatus according to claim 31, wherein the erodible protective coating is a polymer and the level of polymerization increases gradually.

34. An apparatus according to claim 31, wherein the environment also comprises a substance able to react with the active surface.

35. A method according to claim 15, wherein the active surface is an elongated pH sensitive strip, the protective coating is sucrose and the medium is water and further wherein the pH sensitive strip changes color when acid is present in the medium.

36. An apparatus according to claim 21, wherein the active surface is an elongated pH sensitive strip, the protective coating is sucrose and the medium is water and further wherein the pH sensitive strip changes color when acid is present in the medium.

37. A method according to claim 18, wherein the particulate surface is a zeolite, the protective coating is gelatin and the medium is water containing $Ca^{++}$ ions and further wherein the $Ca^{++}$ ions are exchanged for $Na^+$ ions in the zeolite.

38. An apparatus according to claim 24, wherein the particulate surface is a zeolite, the protective coating is gelatin and the medium is water containing $Ca^{++}$ ions and further wherein the $Ca^{++}$ ions are exchanged for $Na^+$ ions in the zeolite.

39. A method according to claim 15, wherein the active surface is an immobilized antibody able to react with an antigen to be detected in the environment.

40. An apparatus according to claim 21, wherein the active surface is an immobilized antibody able to react with an antigen to be detected in the environment.

41. An apparatus providing a continuously available active surface, comprising:
  a. an active surface;
  b. an erodible protective non-uniform coating covering the active surface;

c. means exposing the coated, active surface to the action of an environment comprising a medium able to erode the protective coating; and, wherein the nature of the coating varies so that first portions of the coating are eroded to expose the active surface portions thereunder before other portions are eroded in such a way that portions of the active surface are progressively and gradually exposed as their respective coating portions are eroded thus providing a continuously available active surface.

42. An apparatus according to claim 41, wherein the active surface is one of a surface concentrating agent and a surface reacting agent.

43. An apparatus according to claim 41, wherein the active surface is one of an antigen, an antibody, a receptor, a lectin, an enzyme and a living cell.

44. An apparatus according to claim 41, wherein the active surface is one of a macroreticular resin, a zeolite, a catalyst and an ion exchange resin.

45. An apparatus according to claim 41, wherein the protective coating is selected from the group consisting of dextran, polyacrylamide, polyacrylic acid and its salts, polyvinyl alcohol, polyethylene glycol, polyethylene oxide, polyvinylpyrrolidone, clarified guar gum, carboxymethyl cellulose, hydroxyethyl cellulose, methyl cellulose, algin, carrageenan, xanthan gum, starch, sorbitol, potassium sodium tartrate, mannose and sucrose.

46. An apparatus according to claim 41, wherein the protective coating is a copolymer of maleic anhydride with a vinyl monomer.

47. An apparatus according to claim 41, wherein the environment also comprises a substance able to react with the active surface.

48. An apparatus providing a continuously available active surface comprising:
a. an active surface;
b. an erodible protective non-uniform coating covering the active surface;
c. means exposing the coated, active surface to the action of an environment comprising a medium able to erode the protective coating; and, wherein the thickness of the coating varies so that thinner portions of the coating are eroded to expose the active surface portions thereunder before thicker portions are eroded, in such a way that portions of the active surface are progressively and gradually exposed as their respective coating portions are eroded thus providing a continuously available active surface.

49. An apparatus according to claim 48, wherein the surface is planar, the coating increases in thickness linearly from one end to the other end, and further wherein the reactive surface is first exposed at said one end and is progressively exposed moving towards said other end.

50. An apparatus according to claim 48, wherein the surface is particulate, the thickness of the coating varies in thickness from particle to particle and further wherein the reactive surface is first exposed by eroding the thinner coatings and is progressively exposed as the thicker portions are eroded.

51. An apparatus according to claim 48, wherein the coated particulate surfaces are packed in a tube and the environment acts on the active surface by flowing from one end of the tube to the other.

52. An apparatus according to claim 48, wherein the surface has a tube form and the coating is on the inside of the tube.

53. An apparatus according to claim 48, wherein the environment also comprises a substance able to react with the active surface.

54. An apparatus according to claim 48, wherein the active surface is an elongated pH sensitive strip, the protective coating is sucrose and the medium is water and further wherein the pH sensitive strip changes color when acid is present in the medium.

55. An apparatus according to claim 48, wherein the active surface is an immobilized antibody able to react with an antigen to be detected in the environment.

56. An apparatus according to claim 51, wherein the particulate surface is a zeolite, the protective coating is gelatin and the medium is water containing $Ca^{++}$ ions and further wherein the $Ca^{++}$ ions are exchanged for $Na^{+}$ ions in the zeolite.

57. An apparatus for providing a continuously active surface comprising:
a. an active surface;
b. an erodible protective non-uniform coating covering the active surface;
c. means exposing the coated, active surface to the action of an environment comprising a medium able to erode the protective coating; and, wherein the chemical composition of the coating varies so that first portions of the coating are eroded to expose active surface portions thereunder before other portions are eroded, in such a way that portions of the active surface are progressively and gradually exposed as their respective coating portions are eroded thus providing a continuously available active surface.

58. An apparatus according to claim 57, wherein the concentration of an erodible substance in the protective coating increases gradually.

59. An apparatus according to claim 57, wherein the erodible protective coating is a polymer and the level of polymerization increases gradually.

60. An apparatus according to claim 57, wherein the environment also comprises a substance able to react with the active surface.

* * * * *